US00PP08543P

United States Patent [19]

Cummins et al.

[11] Patent Number: Plant 8,543

[45] Date of Patent: Jan. 18, 1994

[54] FLOWERING CRAB APPLE/APPLE ROOTSTOCK 'GENEVA 65'

[75] Inventors: James N. Cummins; Herbert S. Aldwinckle, both of Geneva, N.Y.

[73] Assignee: Cornell Research Foundation, Inc., Ithaca, N.Y.

[21] Appl. No.: 760,536

[22] Filed: Sep. 16, 1991

[51] Int. Cl.[5] ..... A01H 5/00

[52] U.S. Cl. ..... Plt./34.1

[58] Field of Search ..... Plt. 34.1, 35.2

[56] References Cited

PUBLICATIONS

Cummins, et al, "Proc. 23rd Intern. Hort. Congr." Firenza, 1:1083 (1990).

Cummins et al, "Information Technician Economica Agraria," 9:186–198 (1990).

Cummins et al "Mountaineer Grower," Feb. 20, 1991 pp. 7–13 (1991).

Cummins "Mountaineer Grower" No. 509, pp. 4–8 (1991).

Cummins et al, "Proceedings of the Eighty-Sixth Annual Meeting" pp. 14, 16, 18, 20, 22 and 24 (1991).

Program of the "73rd Meeting of the New York State Fruit Testing Cooperative Associate, Inc." Sep. 19, 1991, lists the official release and naming of 'Geneva 65'.

*Primary Examiner*—James R. Feyrer
*Assistant Examiner*—E. F. McElwain
*Attorney, Agent, or Firm*—Jones, Tullar & Cooper

[57] ABSTRACT

A new and unique apple rootstock 'Geneva 65' that is very dwarfing and resistant to crown rot and fire blight. The tree is also useful as a small ornamental flowering crab.

5 Drawing Sheets

BACKGROUND OF THE INVENTION

The present invention relates to a new and distinct cultivar of apple tree, Geneva 65, which we discovered in a test planting belonging to New York State Agricultural Experiment Station, Cornell University, 'Geneva', Ontario County, N.Y. This discovery is a product of the apple rootstock breeding program of the New York State Agricultural Experiment Station ('Station').

In 1974, pollen was collected from a Beauty Crab apple tree and used to pollinate emasculated flowers of a Malling 27 (M.27) apple tree growing on Station grounds. The seeds were harvested from fruit produced from this cross and were stratified in November, 1974. After stratification, 198 germinating seeds were planted in a Station greenhouse in January, 1975. When the emerging seedlings were about 2.5 cm tall, we inoculated the soil with zoospores of 13 isolates of the fungus *Phytophthora cactorum* which is the causal agent of crown rot. The flat was flooded to mid-hypocotyl level of the seedlings, and kept at about 23° C. for 7 days. All but 54 of the 198 seedlings were killed by this process. The surviving seedlings, when 10 to 15 cm tall, were inoculated in their shoot tips with about $10^6$ cells of isolate Ea273 of the bacterium *Erwinia amylovora*, the causal agent of the of the fire blight disease, using a 26-gauge hypodermic syringe. Four subsequent inoculations with *E. amylovora* isolate Ea273 were made.

We selected 5 *Erwinia amylovora*-resistant seedlings and planted them as trench layers on the Station's Loomis Farm in April, 1976. Rooted liners were harvested in late fall 1979, 1980 and 1981 and were planted in the Station nursery in the springs of 1980, 1981 and 1982 respectively. Maiden trees of the cultivars 'Northern Spy', 'Red Spy', 'Golden Delicious', 'Topred Delicious', 'Summerland McIntosh' and 'Mutsu' were produced by budding onto 'Geneva 65' liners. These trees were subsequently planted in trial orchards at the Station and at the United States Department of Agriculture Appalachian Fruit Research Station, Kearneysville, W.Va.; Hilltop Orchards, Hartford, Mich.; and Highmoor Farm, University of Maine, Monmouth, Me.

In these test plantings, trees on 'Geneva 65' were about 20% smaller than trees on the Malling 9 rootstock, based on comparison with the check trees in the same test plantings. Trees on 'Geneva 65' began flowering very early, usually the second year in the orchard; which was especially noteworthy for 'Northern Spy' and 'Red Spy' cultivars, which at Geneva, N.Y., normally begin fruiting in the 5th or 6th year on the precocity-inducing rootstock Malling-Merton 106. All of the cultivars that have been tested on 'Geneva 65' have demonstrated high production efficiency, equal to that experienced with the Malling 9 rootstock.

COMPATIBILITY

We have experienced no symptoms of incompatibility with 32 trees of the 6 fruiting cultivars mentioned above. Besides these, we have grafted 'Jonagold', 'Melrose', 'Empire' and 'Liberty' cultivars on 'Geneva 65'; in the nursery we have observed no symptoms of incompatibility. All scionwood used was free from known harmful viruses. We have also grafted 'Geneva 65' onto Novole and Malling-Merton 111 rootstocks to produce multiple stock trees with 'Geneva 65' as interstems; we have observed no incompatibility symptoms.

PROPAGATION

We have propagated 'Geneva 65' asexually by budding and grafting onto seedling and clonal rootstocks; by root cuttings; by hardwood cuttings; by greenwood cuttings; by micropropagation; and by conventional layering. These asexual propagules have remained true-to-type will all methods of asexual propagation. We have also used 'Geneva 65' as a seed parent in our breeding program; since 'Geneva 65' is highly heterozygous, its seedlings are much different from the maternal parent and from each other.

DESCRIPTION OF THE INVENTION

Following is a detailed description of our new cultivar 'Geneva 65'Malus cv. Geneva 65. Accompanying figures depict flowering and fruiting habit and fruit characteristics, tree habit, and leaf and shoot characteristics. The numerical color specifications employed are those of The Royal Horticultural Society Colour Chart (1976). Botanical descriptions follow Manual of Cultivated Plants (Bailey, 1949) and Apples of New York (Beach, 1903).

FLOWERS AND FLOWERING

Figure 1:
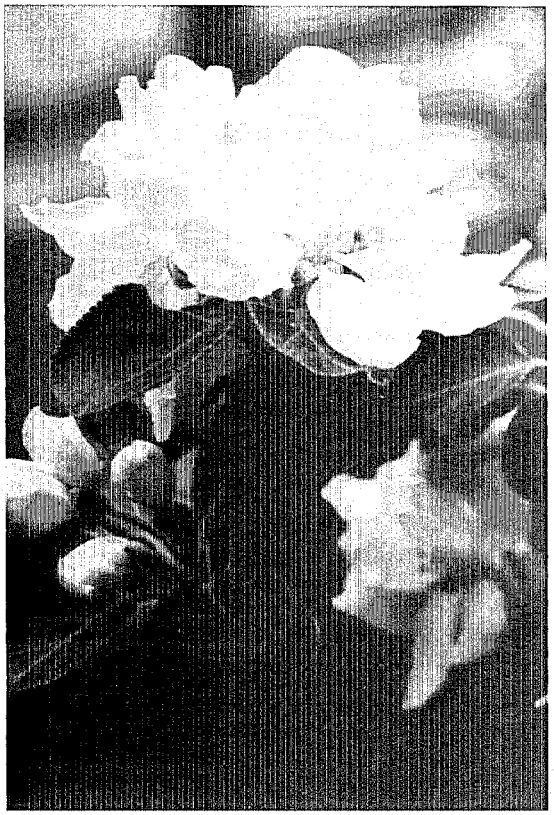
FIG. 1 shows clusters of opened and unopened flowers of 'Geneva 65' (G65).

Flowers are borne on terminals of long shoots, on terminals of spurs, and from axillary buds of long shoots laid down the previous growing season (FIG. 1). Typically, 7 flowers are produced from terminal buds, while 2 to 5 flowers are borne on axillary buds; the axillary buds with only 2 or 3 flowers usually produce no vegetative shoots.

Figure 2:
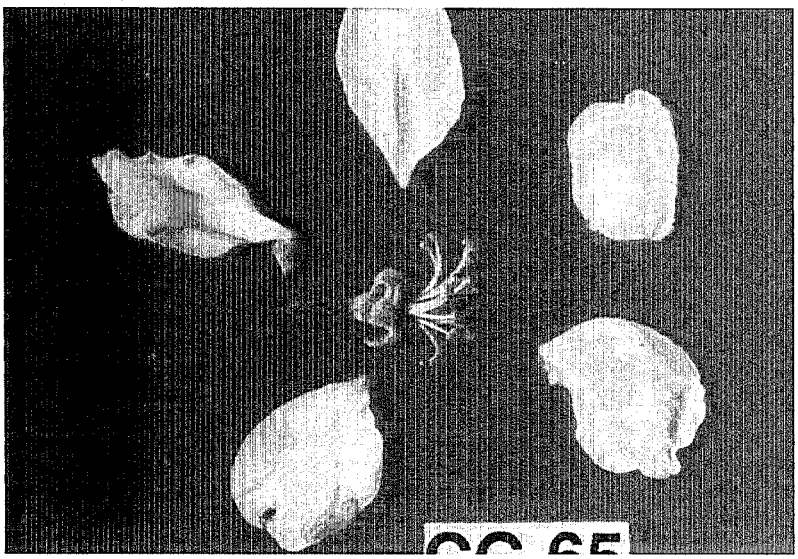
FIG. 2 shows a single flower of 'Geneva 65'.

Flowers are single and very numerous. At full balloon state, the flower is red 48B, opening to white 155B and with red 49C on much of the abaxial surface. Structurally the flowers are typical of Malus, with a 5-lobed calyx, 5 petals, 5 pistils, and about 20 stamens; each carpel usually has 2 ovules (FIG. 2). Flowers average about 22 mm diameter. Pedicels are short (25–30 mm) and stiff. Pollen is yellow-orange 15A, very abundant, germinates rapidly, and is long-lived in frozen storage.

FRUITING HABIT AND FRUIT

Flowers of 'Geneva 65' are highly fertile, setting 50 to 100% of flowers pollinized with viable pollen. No "June drop" of fruit has been observed; fruits that have been fertilized are carried to maturity. Fruits are therefore borne in clusters of 2 to as many as 7 per peduncle. A tree of 'Geneva 65' that has carried an excessive crop produced no or few flowers the following year.

Figure 3:
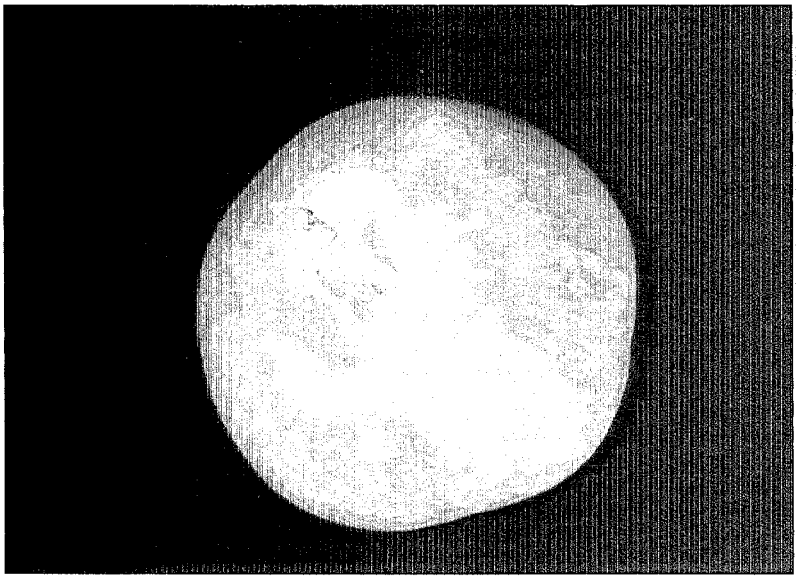
FIG. 3 shows fruit of 'Geneva 65'.
Figure 4:
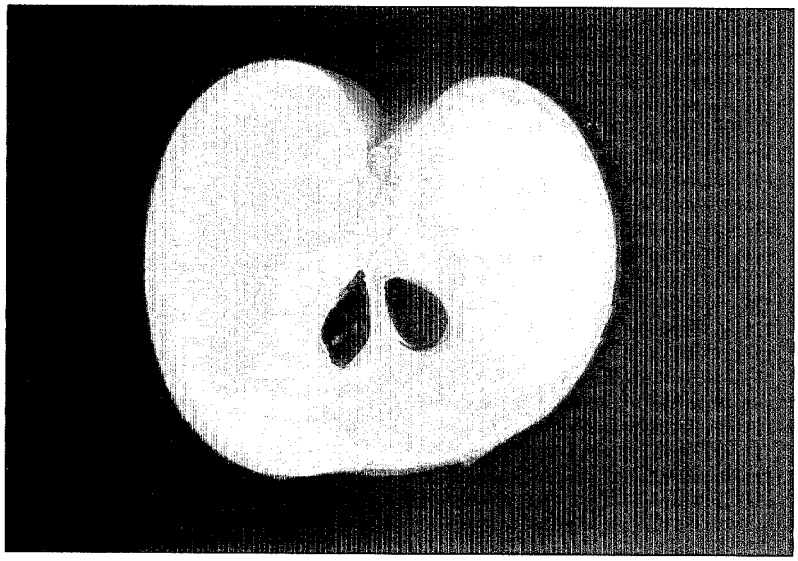
FIG. 4 shows a longisection of fruit of 'Geneva 65', showing typical acuminate seeds.
Figure 6:
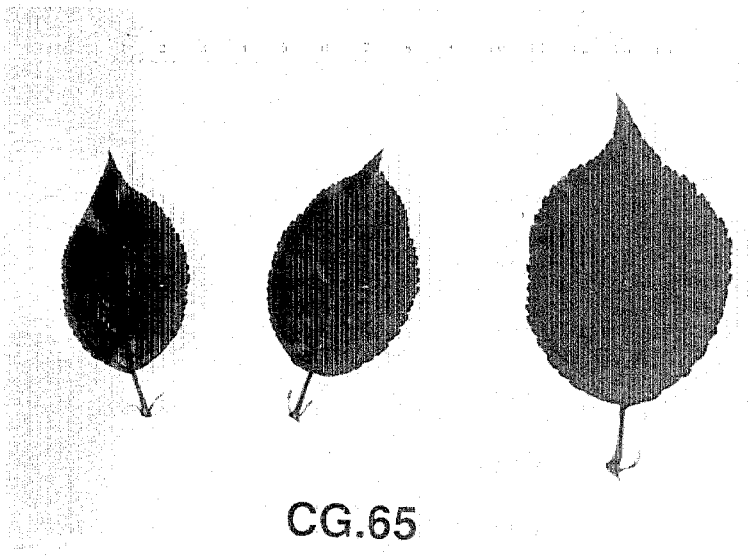
FIG. 6 shows leaves of 'Geneva 65', showing typical minute stipules, short petioles, cuspidate to nearly aristate tips, obtuse bases, and coarsely serrate margins.
Figure 5:
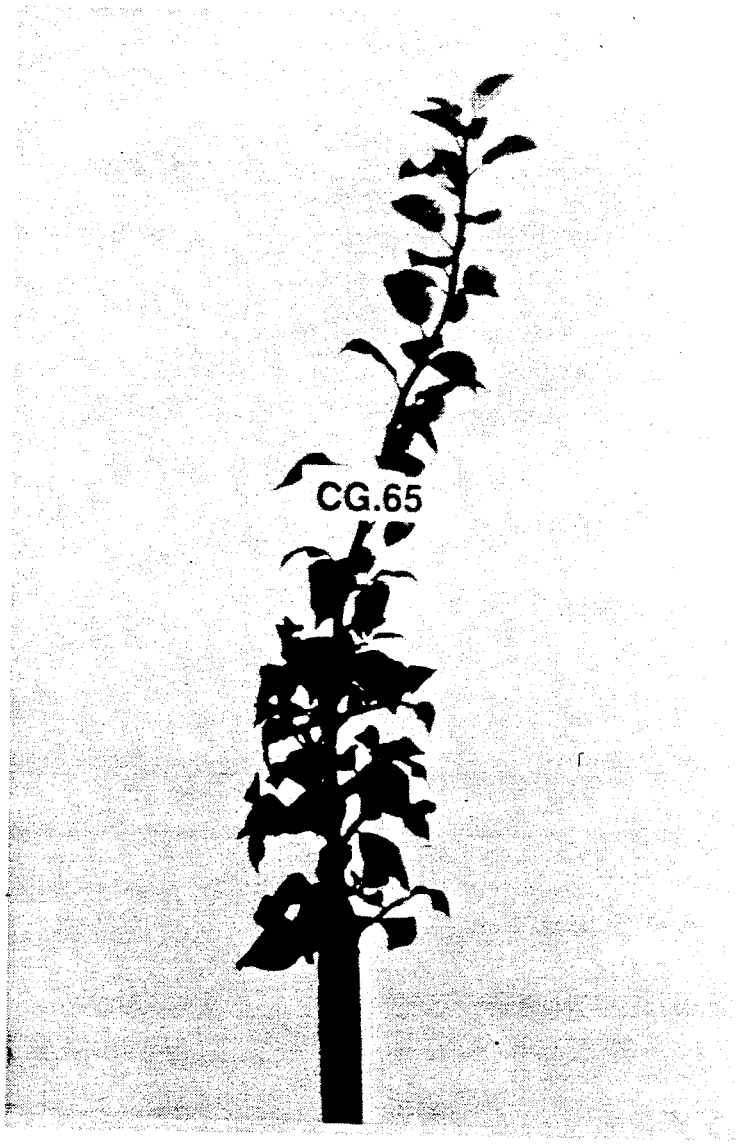
FIG. 5 shows a two-year-old shoot of 'Geneva 65'. Short spurry shoots are numerous on older wood and branches are few.
Figure 7:
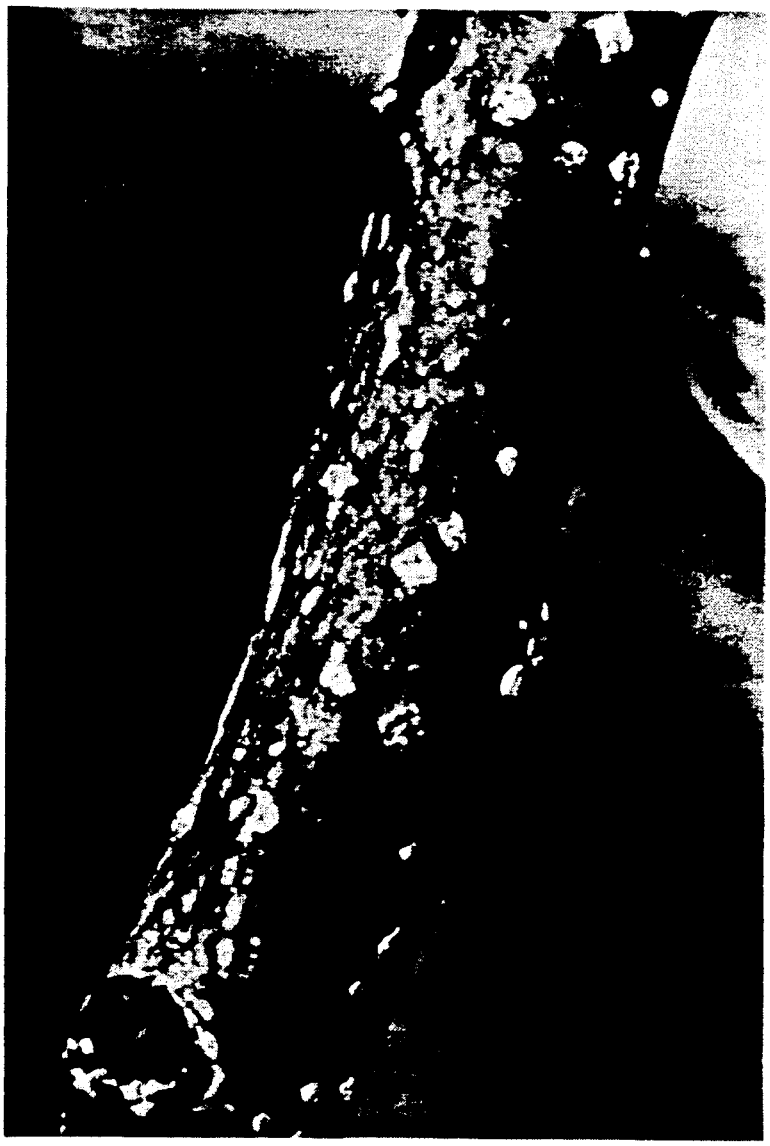
FIG. 7 show a two-year-old shoot of 'Geneva 65', showing lenticels slightly raised, oval.

The individual fruits are round to roundish oblate, symmetrical, regular, usually without residual calyx or retained stamens (FIGS. 3 and 4). Fruits are about 20 mm diameter × 18 mm long. Cavity is medium in depth and breadth, regular, often with light concentric russetting. Pedicels are short (25–30 mm), moderately thick and stiff. Lenticels on fruit are white, small, round, very slightly raised. Where exposed to sun, skin color is from red 38D to 48A on green-white 157C ground with light bloom. Flesh is yellow-orange 23B; very firm; moderate texture; acid and astringent. Seeds are medium in size, 5.5 mm long × 3.5 mm wide; usually 2 per carpel; dark brown; usually acuminate.

TREE HABIT

The unbudded tree of 'Geneva 65' is a small shrub, typically standing about 1.5 m tall × about 1 m wide. There is no single dominant trunk, but rather 15 to 30 shoots arising from the roots. The unbudded tree is a dwarf, comparable to a Malling 9 apple tree of similar age. Growth rate is slow, with very early cessation of growth typically occurring about 2 weeks earlier than for Malling 9. Some suckers are produced but the numbers are small and they are not exuberant.

SHOOTS

Adventitious shoots arising from roots, presumably juvenile, exhibit numerous spines typically 3 to 7 or 8 cm long for the basipetal 10 to 20 nodes; spines are uncommon on mature-phase shoots. In tissue culture, the most basipetal 1 or 2 leaves displayed on a new shoot may be deeply incised, almost trilobate and similar in shape to *Malus sargentii.*

Matured shoots of current season are greyed-orange 175A; older shoots become darker brown to 166B. Shoots are quite short, usually less than 20 cm, with short internodes, usually about 12–15 mm. Axillary buds are obtuse, sessile, usually somewhat appressed; most carry both vegetative and flower primordia; bud scales moderately large, lightly tomentose. Lenticels are oval, medium in size, slightly raised, greyed-yellow 161C on new shoots. Burrknots are not commonly observed but do occur occasionally on shoots 3 or more years old. No sphaeroblasts have been observed. Spring budbreak is midseason, after Novole, with Malling 9 and several days before Malling 26. Autumn leaffall is moderately early. Wood is not brittle as is that of Malling 9.

Timing of budbreak, blooming, maturing fruit and leaffall vary over a range of about 30 days at a given location and there is of course wide variation in related to climatic differences; therefore calendar dates for these events would have no significance. The most useful descriptions are those which relate G.65 to a common standard, such as Malling 9. However, it should be noted that only budbreak and leaffall are likely to be useful, since flowers and fruit will rarely be observed on these plants.

Relative to Malling 9, budbreak of G.65 is similar ±2 days; full bloom of G.65 is usually 2 or 3 days earlier than M.9; fruit of G.65 matures about 45 days after M.9; in the nursery, cessation of active shoot extension of G.65 is variable but 10 to 15 days before M.9; leaffall of G.65 is similar to M.9 to a week later than M.9.

LEAVES

Lamella is ovate, tip cuspidate to nearly aristate, usually acuminate, margin is waxy; typically lamella for mature midshoot leaf will be approximately 5 cm long and 2 cm wide leaf; margin coarsely serrate, 6 to 8 serrations per cm; base obtuse, usually symmetrical, stipules absent or, rarely, minute. Adaxial lamella surface green 137A–B; abaxial surface yellow-green 147C; both surfaces glabrous, dull, with a few hairs on major veins. Petiole 15–20 mm long, slender. Leaf poise typically 35°–40° from shoot.

USEFULNESS

'Geneva 65' is a very dwarfting rootstock for apples it is resistant to crown rot and to fire blight, diseases that are limiting in many parts of the United States. In the orchard, anchorage of grafted trees is similar to that of trees on Malling 26, but because of the precocity induced by 'Geneva 65' permanent support is strongly suggested.

'Geneva 65' also has promise as a disease-resistant interstem for apple.

Because the unbudded tree is a small, slow-growing shrub, 'Geneva 65' can be used as an own-rooted ornamental flowering crab in locations in which resistance to fire blight is especially important.

We claim:

1. A new and distinct cultivar of apple tree, substantially as shown and described herein, characterized particularly as to novelty by being a very dwarfing rootstock that is resistant to crown rot and to fire blight.

* * * * *

CG.65